United States Patent
Nguyen et al.

(10) Patent No.: US 11,583,671 B2
(45) Date of Patent: Feb. 21, 2023

(54) HEART PUMP CUFF

(71) Applicant: TC1 LLC, St. Paul, MN (US)

(72) Inventors: John Duc Nguyen, San Ramon, CA (US); Huy Ngo, San Jose, CA (US); Carine Hoarau, Lafayette, CA (US); Fabian Franco, Livermore, CA (US)

(73) Assignee: TC1 LLC, St. Paul, MN (US)

( * ) Notice: Subject to any disclaimer, the term of this patent is extended or adjusted under 35 U.S.C. 154(b) by 54 days.

(21) Appl. No.: 17/140,286

(22) Filed: Jan. 4, 2021

(65) Prior Publication Data

US 2021/0121677 A1    Apr. 29, 2021

Related U.S. Application Data

(62) Division of application No. 15/681,880, filed on Aug. 21, 2017, now Pat. No. 10,894,116.
(Continued)

(51) Int. Cl.
*A61M 60/859*    (2021.01)
*A61M 60/148*    (2021.01)
(Continued)

(52) U.S. Cl.
CPC ........ *A61M 60/148* (2021.01); *A61M 60/178* (2021.01); *A61M 60/183* (2021.01);
(Continued)

(58) Field of Classification Search
CPC . A61M 60/857; A61M 60/859; A61M 60/863
See application file for complete search history.

(56) References Cited

U.S. PATENT DOCUMENTS 3,766,567 A    10/1973  Kahn et al.
4,099,759 A    7/1978   Kornhauser
(Continued)

FOREIGN PATENT DOCUMENTS

CA    2526920    2/2009
CN    1842354    10/2006
(Continued)

OTHER PUBLICATIONS

"Nickel Titanium", Wikipedia, Available online at: https://en.wikipedia.org/wiki/Nickel_titanium, Accessed from internet at Jul. 28, 2016, 9 pages.
(Continued)

*Primary Examiner* — George R Evanisko
(74) *Attorney, Agent, or Firm* — Kilpatrick Townsend & Stockton LLP

(57) ABSTRACT

At least some embodiments of the disclosure may advantageously limit bleeding and the occurrence of blood leaks after heart pump implantation. In some embodiments, a base may be provided that includes a flexible layer mechanically coupled with a conduit. The flexible layer may be coupled with the proximal end of the conduit. The conduit may be configured to receive a cannula of the heart pump therethrough. The outer surface of the conduit may be configured to engage a surface of the heart formed after coring the heart. The conduit may be metal and may have a flared and/or beveled distal end. The conduit may be a flexible material. A distal flexible layer may be provided at a distal end of the conduit that is configured to engage with an inner surface of the heart.

20 Claims, 7 Drawing Sheets

Related U.S. Application Data

(60) Provisional application No. 62/377,908, filed on Aug. 22, 2016.

(51) Int. Cl.
*A61M 60/178* (2021.01)
*A61M 60/183* (2021.01)
*A61M 60/863* (2021.01)
*A61M 60/232* (2021.01)
*A61M 60/473* (2021.01)

(52) U.S. Cl.
CPC ........ *A61M 60/232* (2021.01); *A61M 60/859* (2021.01); *A61M 60/863* (2021.01); *A61M 60/473* (2021.01)

(56) References Cited

U.S. PATENT DOCUMENTS

| | | | |
|---|---|---|---|
| 4,458,366 A | 7/1984 | MacGregor | |
| 4,688,998 A | 8/1987 | Olsen et al. | |
| 4,769,031 A | 9/1988 | McGough et al. | |
| 5,055,005 A | 10/1991 | Kletschka | |
| 5,084,064 A * | 1/1992 | Barak | A61M 60/196 623/1.31 |
| 5,089,014 A * | 2/1992 | Holfert | A61B 17/11 623/1.24 |
| 5,098,369 A | 3/1992 | Heilman et al. | |
| 5,139,517 A | 8/1992 | Corral | |
| 5,195,877 A | 3/1993 | Kletschka | |
| 5,222,980 A | 6/1993 | Gealow | |
| 5,275,580 A | 1/1994 | Yamazaki | |
| 5,456,714 A | 10/1995 | Owen | |
| 5,470,208 A | 11/1995 | Kletschka | |
| 5,613,935 A | 3/1997 | Jarvik | |
| 5,708,346 A | 1/1998 | Schob | |
| 5,814,005 A | 9/1998 | Barra et al. | |
| 5,827,316 A | 10/1998 | Young et al. | |
| 5,843,088 A | 12/1998 | Barra et al. | |
| 5,984,956 A | 11/1999 | Tweden et al. | |
| 6,001,056 A | 12/1999 | Jassawalla et al. | |
| 6,050,975 A | 4/2000 | Poirier | |
| 6,066,085 A | 5/2000 | Heilman et al. | |
| 6,146,325 A | 11/2000 | Lewis et al. | |
| 6,238,334 B1 | 5/2001 | Easterbrook, III et al. | |
| 6,254,564 B1 | 7/2001 | Wilk et al. | |
| 6,290,639 B1 * | 9/2001 | Mussivand | A61M 60/178 600/16 |
| 6,346,071 B1 | 2/2002 | Mussivand | |
| 6,390,976 B1 | 5/2002 | Spence et al. | |
| 6,669,708 B1 | 12/2003 | Nissenbaum et al. | |
| 6,673,043 B1 | 1/2004 | Landesberg | |
| 6,689,147 B1 | 2/2004 | Koster, Jr. | |
| 6,705,988 B2 | 3/2004 | Spence et al. | |
| 6,726,648 B2 | 4/2004 | Kaplon et al. | |
| 6,732,501 B2 | 5/2004 | Yu et al. | |
| 6,802,806 B2 | 10/2004 | McCarthy et al. | |
| 6,808,498 B2 | 10/2004 | Laroya et al. | |
| 6,863,677 B2 | 3/2005 | Breznock | |
| 6,942,672 B2 | 9/2005 | Heilman et al. | |
| 6,994,666 B2 | 2/2006 | Shannon et al. | |
| 7,018,384 B2 | 3/2006 | Skakoon | |
| 7,048,681 B2 | 5/2006 | Tsubouchi et al. | |
| 7,056,286 B2 | 6/2006 | Ravenscroft et al. | |
| 7,077,801 B2 | 7/2006 | Haverich | |
| 7,214,234 B2 | 5/2007 | Rapacki et al. | |
| 7,303,553 B2 | 12/2007 | Ott | |
| 7,404,792 B2 | 7/2008 | Spence et al. | |
| 7,462,019 B1 | 12/2008 | Allarie et al. | |
| 7,824,358 B2 | 11/2010 | Cotter et al. | |
| 8,152,845 B2 | 4/2012 | Bourque | |
| 8,343,028 B2 | 1/2013 | Gregoric et al. | |
| 8,480,657 B2 | 7/2013 | Bakos et al. | |
| 8,500,759 B2 | 8/2013 | Koyfman et al. | |
| 8,579,790 B2 | 11/2013 | Jeffery et al. | |
| 8,870,739 B2 | 10/2014 | LaRose et al. | |
| 8,894,561 B2 | 11/2014 | Callaway et al. | |
| 9,144,637 B2 | 9/2015 | Callaway et al. | |
| 9,186,447 B2 | 11/2015 | Callaway et al. | |
| 9,199,019 B2 | 12/2015 | Callaway et al. | |
| 9,387,285 B2 | 7/2016 | Callaway et al. | |
| 9,750,858 B2 | 9/2017 | Callaway et al. | |
| 9,981,076 B2 | 5/2018 | Callaway et al. | |
| 9,981,077 B2 | 5/2018 | Callaway et al. | |
| 10,111,993 B2 | 10/2018 | Callaway et al. | |
| 2002/0045846 A1 | 4/2002 | Kaplon et al. | |
| 2002/0095210 A1 * | 7/2002 | Finnegan | A61M 60/216 623/1.36 |
| 2003/0023255 A1 | 1/2003 | Miles et al. | |
| 2003/0040765 A1 | 2/2003 | Breznock | |
| 2003/0130668 A1 | 7/2003 | Nieman et al. | |
| 2004/0002624 A1 | 1/2004 | Yu et al. | |
| 2004/0054251 A1 | 3/2004 | Liotta | |
| 2004/0153112 A1 | 8/2004 | Nissenbaum et al. | |
| 2004/0171905 A1 | 9/2004 | Yu et al. | |
| 2004/0193004 A1 | 9/2004 | Tsubouchi et al. | |
| 2004/0236170 A1 | 11/2004 | Kim | |
| 2005/0033107 A1 | 2/2005 | Tsubouchi | |
| 2005/0101982 A1 | 5/2005 | Ravenscroft et al. | |
| 2005/0131451 A1 | 6/2005 | Kleshinski et al. | |
| 2005/0149093 A1 | 7/2005 | Pokorney | |
| 2005/0154411 A1 | 7/2005 | Breznock et al. | |
| 2005/0209502 A1 | 9/2005 | Schmid et al. | |
| 2005/0251187 A1 | 11/2005 | Beane et al. | |
| 2006/0036313 A1 | 2/2006 | Vassiliades | |
| 2006/0089707 A1 | 4/2006 | Vassiliades et al. | |
| 2006/0099716 A1 | 5/2006 | Tipler et al. | |
| 2006/0142634 A1 | 6/2006 | Anstadt et al. | |
| 2006/0161193 A1 | 7/2006 | Beane et al. | |
| 2007/0088375 A1 | 4/2007 | Beane et al. | |
| 2007/0100363 A1 | 5/2007 | Dollar et al. | |
| 2007/0106315 A1 | 5/2007 | Gregoric et al. | |
| 2007/0134993 A1 | 6/2007 | Tamez et al. | |
| 2007/0167968 A1 | 7/2007 | Pandey | |
| 2007/0167969 A1 | 7/2007 | Pandey | |
| 2007/0173879 A1 | 7/2007 | Pandey | |
| 2007/0197855 A1 | 8/2007 | Richardson et al. | |
| 2007/0208290 A1 | 9/2007 | Pecor et al. | |
| 2007/0265643 A1 | 11/2007 | Beane et al. | |
| 2008/0009668 A1 | 1/2008 | Cohn | |
| 2008/0009887 A1 | 1/2008 | Cohn | |
| 2008/0009891 A1 | 1/2008 | Cohn | |
| 2008/0076959 A1 | 3/2008 | Farnan et al. | |
| 2009/0012552 A1 | 1/2009 | Pandey et al. | |
| 2009/0082792 A1 | 3/2009 | Koyfman et al. | |
| 2009/0143638 A1 | 6/2009 | Keogh et al. | |
| 2009/0171136 A1 | 7/2009 | Shambaugh, Jr. | |
| 2010/0305692 A1 | 12/2010 | Thomas et al. | |
| 2011/0118766 A1 | 5/2011 | Reichenbach et al. | |
| 2011/0118829 A1 | 5/2011 | Hoarau et al. | |
| 2011/0118833 A1 | 5/2011 | Reichenbach et al. | |
| 2011/0144680 A1 | 6/2011 | Nguyen et al. | |
| 2011/0160850 A1 | 6/2011 | Bourque | |
| 2011/0245582 A1 | 10/2011 | Zafirelis et al. | |
| 2012/0010455 A1 | 1/2012 | Reichenbach et al. | |
| 2012/0035411 A1 | 2/2012 | LaRose et al. | |
| 2012/0046514 A1 | 2/2012 | Bourque | |
| 2012/0059212 A1 | 3/2012 | LaRose et al. | |
| 2012/0059398 A1 * | 3/2012 | Pate | A61M 60/863 606/153 |
| 2012/0165931 A1 | 6/2012 | Bourque | |
| 2012/0226096 A1 | 9/2012 | Callaway et al. | |
| 2013/0060267 A1 * | 3/2013 | Farnan | A61M 60/221 606/153 |
| 2013/0261375 A1 | 10/2013 | Callaway et al. | |
| 2014/0067057 A1 | 3/2014 | Callaway et al. | |
| 2015/0133719 A1 | 5/2015 | Callaway et al. | |
| 2015/0273124 A1 | 10/2015 | Callaway et al. | |
| 2015/0335802 A1 | 11/2015 | Callaway et al. | |
| 2016/0038664 A1 | 2/2016 | Callaway et al. | |
| 2016/0051738 A1 | 2/2016 | Callaway et al. | |
| 2016/0121033 A1 | 5/2016 | Cotter et al. | |

(56) References Cited

U.S. PATENT DOCUMENTS

| | | | |
|---|---|---|---|
| 2017/0326281 A1 | 11/2017 | Callaway et al. | |
| 2018/0243488 A1 | 8/2018 | Callaway et al. | |

FOREIGN PATENT DOCUMENTS

| | | |
|---|---|---|
| DE | 20202883 | 7/2002 |
| DE | 10108809 | 9/2002 |
| EP | 1706168 | 10/2006 |
| EP | 2822614 | 1/2015 |
| EP | 2822614 | 3/2016 |
| JP | 2006528304 | 12/2006 |
| JP | 2007510522 | 4/2007 |
| JP | 2013510691 | 3/2013 |
| JP | 2015512687 | 4/2015 |
| WO | 0074747 | 12/2000 |
| WO | 03001980 | 1/2003 |
| WO | 2004014456 | 2/2004 |
| WO | 2005046783 | 5/2005 |
| WO | 2005051838 | 6/2005 |
| WO | 2007038109 | 4/2007 |
| WO | 2008131453 | 10/2008 |
| WO | 2009085243 | 7/2009 |
| WO | 2011060386 | 5/2011 |
| WO | 2011081629 | 7/2011 |
| WO | 2012051454 | 4/2012 |
| WO | 2012119073 | 9/2012 |
| WO | 2013056131 | 4/2013 |
| WO | 2013064529 | 5/2013 |
| WO | 2013134319 | 9/2013 |
| WO | 2014036060 | 3/2014 |
| WO | 2014144085 | 9/2014 |
| WO | 2014149892 | 9/2014 |
| WO | 2015134944 | 9/2015 |

OTHER PUBLICATIONS

Barletta et al., "Design of a Bearing Less Blood Pump", Proc.Third International Symposium on Magnetic Suspension Technology, Jul. 1, 1996, pp. 265-274.

Thompson , "An Overview of Nickel-Titanium Alloys Used in Dentistry", International Endodontic Journal, vol. 33, Jul. 2000, pp. 297-310.

* cited by examiner

HEART PUMP CUFF

CROSS-REFERENCES TO RELATED APPLICATIONS

The present application is a Divisional of U.S. patent application Ser. No. 15/681,880 filed Aug. 21, 2017 (Allowed); which claims the benefit of U.S. Provisional Appln No. 62/377,908 filed Aug. 22, 2016, the full disclosures which are incorporated herein by reference in their entirety for all purposes.

BACKGROUND

The present disclosure is generally related to medical systems, devices, and methods for treating a heart of a patient. In particular, heart pump systems, devices, and implantation methods are provided. At least some embodiments of the disclosure may advantageously facilitate implantation and/or limit bleeding and the occurrence of blood leaks after heart pump implantation.

Mechanical circulatory support (MCS) systems assist the heart in circulating blood in the body. A ventricular assist device (VAD) is an example of an MCS system that is used to assist one or both ventricles of the heart to circulate blood. For patients suffering from heart failure, assisting the left ventricle of the heart via a left ventricular assist device (LVAD) extending between the left ventricle and the aorta is more common, although the right ventricle may be assisted via a right ventricular assist device (RVAD) extending between the right ventricle and the pulmonary artery. Two VADs can also be used in a BiVAD configuration. Currently, VADs are commonly used for destination therapy or as a bridge to transplant option for patients with heart failure.

According to current techniques for LVAD implantation, a hole is formed in the heart wall, typically at or near the apex of the left ventricle, and a connector or conduit is secured within or about the hole. RVAD implantation techniques involve forming a hole in the lateral wall of the right ventricle and securing a connector or conduit within or about the hole. After establishing a fluid tight connection between the conduit and the ventricular wall, an inlet tube of the VAD is attached to the connector or conduit, which allows blood to flow from the ventricle to a pump of the VAD. A drawback of certain conventional LVAD systems is that it takes a period of time for sufficient endothelialization and tissue ingrowth to occur. In the meantime the patient is at heightened risk of bleeding around the pump inflow and other risks. The pump can also become misaligned or prolapse.

While existing techniques are largely successful, further improvements may be desired. There is the need for devices and methods to facilitate less invasive implantation approaches. There is the need for devices and methods to reduce adverse events associated with existing implantation procedures.

BRIEF SUMMARY

The present disclosure is generally related to medical systems, devices, and methods for treating a heart of a patient. In particular, heart pump systems, devices, and implantation methods are provided. At least some embodiments of the disclosure may advantageously limit bleeding and the occurrence of blood leaks after heart pump implantation. As mentioned above, heart pump implantation systems, devices, and methods may benefit from establishing a fluid tight connection between the conduit or connector and the ventricular wall. In some implantation procedures, the fluid tight connection between the conduit and ventricular wall may be established during an "on-pump" procedure where a cardiopulmonary bypass is employed and where the heart is stopped from beating. In other procedures, the fluid tight connection may be attempted during an "off-pump" procedure where a cardiopulmonary bypass is not employed (e.g., to avoid risks of cardiopulmonary bypasses) and the heart is continually beating. The fluid tight connection may be established during implantation, however, under certain conditions, tissue bleeding and/or the occurrence of blood leaks at system component connections or device tissue interfaces may occur sometime after heart pump implantation before the site has sufficiently healed. The tissue bleeding or blood leaking at the component connections may be in-part due to the fact that the heart is constantly pumping and moving after heart pump implantation. Accordingly, even if a fluid tight connection is established during the implantation procedure, such a connection may be temporary and may weaken sometime after completion of the implantation procedure. Embodiments of the present disclosure may help limit or otherwise reduce tissue bleeding and/or blood leaking after such procedures.

In some aspects of the present disclosure, a method of coupling a heart pump to a heart of a patient may be provided. The method may include coring an opening in the heart. The opening may extend from an outside surface of the heart to an inside surface of the heart. A base may be sutured to the heart. The base may comprise a flexible layer mechanically coupled with a conduit. The flexible layer may be configured to engage the outer surface of the heart. The conduit may have a central axis, a proximal end, a distal end, an inner surface, and an outer surface. The flexible layer may be coupled with the proximal end of the conduit. The conduit may be configured to receive a cannula of the heart pump therethrough along the central axis of the conduit and from the proximal end to the distal end of the conduit. The inner surface of the conduit may be configured to engage with the cannula and the outer surface of the conduit may be configured to engage a surface of the heart formed after coring the heart. A port may be coupled to the base. The port may comprise an engagement feature for coupling with the heart pump. The inflow cannula of the heart pump may be inserted through the conduit of the base. Thereafter, the heart pump may be coupled with the engagement feature of the port.

In some embodiments, the opening of the heart may be cored after the base is attached to the heart.

In some embodiments, the conduit may be a metal material and the conduit may be sewn, bonded, glued, welded, or crimped to the flexible layer.

Optionally, the flexible layer comprises a felt material. In some embodiments, the flexible layer comprises a graft material. In some embodiments, the flexible layer comprises polyester.

Optionally, the inner surface of the conduit may taper away from the central axis of the conduit and toward the outer surface of the conduit at the distal end of the conduit to form a beveled distal edge of the conduit.

In some embodiments, the outer surface of the conduit may taper away from the central axis of the conduit at the distal end of the conduit to form a flared distal end.

In still further embodiments, the conduit may be a flexible material.

The base may be sewn, sutured, or otherwise attached to the heart by sewing through the flexible layer, through the outer surface of the heart, through the surface of the heart formed after coring the heart, and through the flexible conduit.

In some embodiments, the base may include a distal flexible layer coupled with the distal end of the conduit. The distal flexible layer may be configured to engage with an inner surface of the heart disposed about the cored opening in the heart. Optionally, the base may be sewn to the heart by sewing through the flexible layer, through the outer surface of the heart, through the inner surface of the heart and through the distal flexible layer.

In some embodiments, the port may include a second flexible layer. The port may be coupled to the base by sewing the second flexible layer of the port to the flexible layer of the base.

In some embodiments, the heart pump may include an engagement feature corresponding with the engagement feature of the port. A flexible layer may be disposed between the engagement feature of the heart pump and the engagement feature of the port when the heart pump is coupled with the engagement feature of the port.

In further aspects of the present disclosure, a heart pump system may be provided that includes a base comprising a flexible layer mechanically coupled with a conduit. The flexible layer may be configured to engage an outer surface of a heart. The conduit may have a central axis, a proximal end, a distal end, an inner surface, and an outer surface. The flexible layer may be coupled with the proximal end of the conduit. The conduit may be configured to receive a cannula of the heart pump therethrough along the central axis of the conduit and from the proximal end to the distal end of the conduit. The inner surface of the conduit may be configured to engage a surface of the heart formed after coring the heart. A port may be configured to couple with the base. The port may include an engagement feature for coupling with the heart pump.

The conduit may be a metal material, and the conduit may be sewn, bonded, or crimped to the flexible layer. The flexible layer may be a felt material. Optionally, the flexible layer may be a graft material.

In some embodiments, the inner surface of the conduit may taper away from the central axis of the conduit and toward the outer surface of the conduit at the distal end of the conduit to form a beveled distal edge of the conduit. The outer surface of the conduit may taper away from the central axis at the distal end of the conduit to form a flared distal end.

The conduit may be a flexible material in some embodiments. Optionally, the base may include a distal flexible layer coupled with the distal end of the conduit. The distal flexible layer may be configured to engage with an inner surface of the heart disposed about a cored opening in the heart.

The port may include a second flexible layer. Optionally, the port may be configured to couple to the base by sewing the second flexible layer to the flexible layer of the base.

In some embodiments, a flexible layer may be coupled with a proximal side of the engagement feature of the port such that the flexible layer is sandwiched between the engagement feature of the port and the heart pump when the heart pump is coupled with the engagement feature of the port.

In some embodiments, the heart pump system may further include the heart pump. The heart pump may include an engagement feature corresponding to the engagement feature of the port. The heart pump may further include an inflow cannula configured to be inserted through the conduit of the base.

In still further embodiments, a heart pump system may be provided that may include a heart pump having an inlet and an outlet. An inflow cannula may be provided having a proximal end and a distal end. The proximal end of the inflow cannula may be coupled with the inlet of the heart pump. A flexible layer may be disposed between the inflow cannula and the heart pump.

Optionally, the inflow cannula may include an engagement feature for coupling with the inlet of the heart pump. The engagement feature may have a surface covered with the flexible layer.

In some embodiments, the inflow cannula comprises an engagement feature for coupling with a cuff. The engagement feature may have a surface covered with a second flexible layer such that the flexible layer is disposed between the inflow cannula and the cuff when the inflow cannula couples with the cuff.

The heart pump system may further include the cuff. The cuff may include a port and a base. The inflow cannula may be configured to couple with the port of the cuff.

In some embodiments, the engagement feature comprises a flange disposed between the proximal end and the distal end of the inflow cannula.

Embodiments of the disclosure covered by this patent are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

BRIEF DESCRIPTION OF THE DRAWINGS

Further details, aspects, and embodiments of the disclosure will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION

The present disclosure is generally related to medical systems, devices, and methods for treating a heart of a patient. At least some embodiments of the disclosure may advantageously limit tissue bleeding and the occurrence of blood leaks after heart pump implantation.

Figure 1:
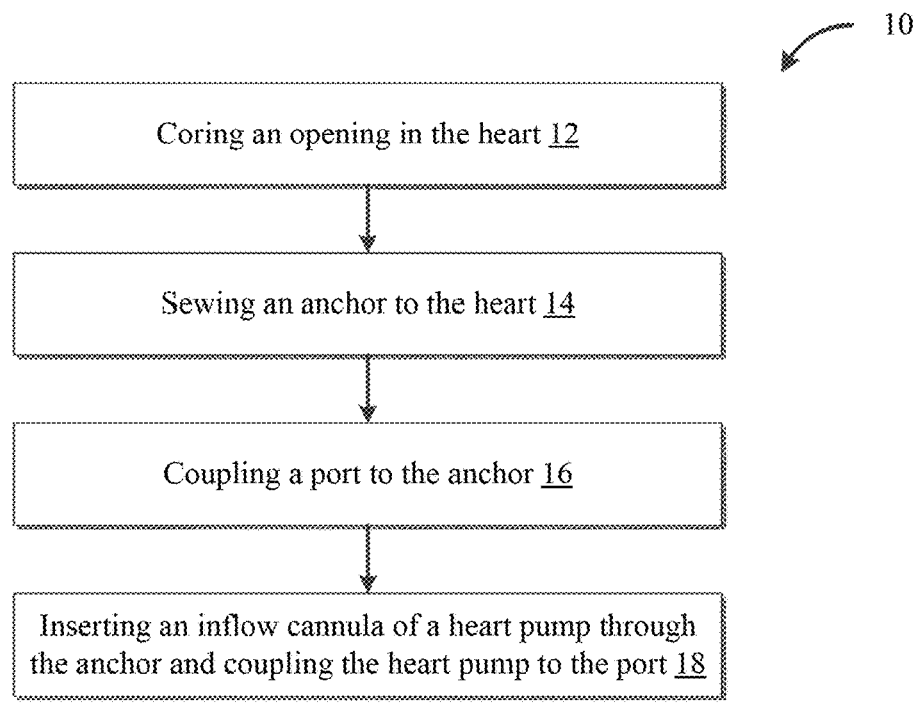
FIG. 1 illustrates an exemplary heart pump implantation method according to some embodiments of the present disclosure.

FIG. 1 illustrates an exemplary heart pump implantation method 10 according to some embodiments of the present disclosure. The method 10 may include coring an opening in the heart of a patient 12. A base may be sewn to the heart 14. A port may be coupled with the base 16. Thereafter, an inflow cannula of a heart pump may be inserted through the base and the heart pump may be coupled with the port 18.

Method 10 may be utilized to treatment patients suffering from heart failure. For example, in some embodiments, a left ventricular assist device (LVAD) may be implanted according to method 10 to assist the left ventricle of the heart of a patient. The heart pump may pump blood from the left ventricle to the patient's aorta. In some embodiments, the right ventricle may be assisted by implanting a right ventricular assist device (RVAD) according to method 10 to pump blood from the right ventricle and the pulmonary artery. Additionally, in some embodiments, two VADs may be implanted according to method 10 to provide BiVAD support to a patient.

Advantageously, method 10 may limit the occurrence of tissue bleeding and/or blood leaking during the implantation procedure and after the heart pump is successfully installed. Such bleeding may occur between component parts and/or along the sheath or circumference. In particular, embodiments of method 10 may limit blood leaking at the interface between the port and the heart pump, at the interface between the port and the base, and/or at the interface between the base and the heart. Additionally, some embodiments, may limit tissue bleeding after pump implantation.

While the method is described above and illustrated in a particular order, it should be understood that this should not be interpreted as implying that the above described and illustrated order is critical. For example, in some embodiments, the base may be sewn to the heart 14 prior to coring an opening in the heart 12. Similarly, in some embodiments, the port may be coupled with the base 16 prior to sewing the base to the heart 14. As such, in certain embodiments, the opening in the heart 12 may be cored after coupling the port with the base 16.

Figure 2:
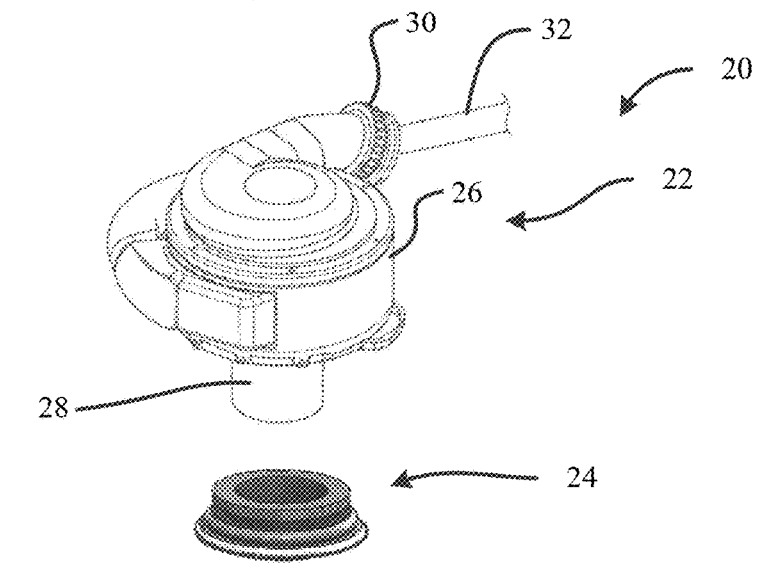
FIG. 2 illustrates an exemplary heart pump system according to some embodiments of the present disclosure.
Figure 2:
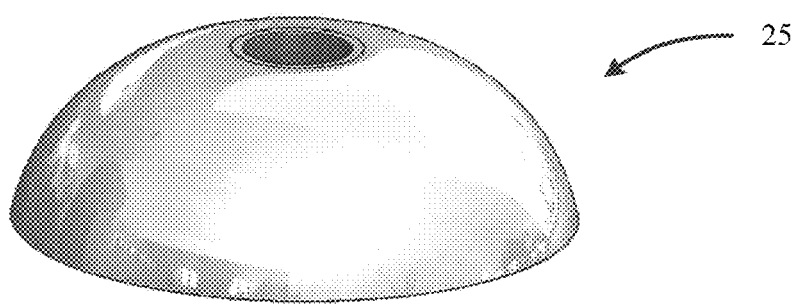

FIG. 2 illustrates an exemplary heart pump system 20 that may be used to carry out method 10 according to some embodiments of the present disclosure. Heart pump system 20 may include a heart pump 22 and a heart pump cuff 24 for coupling the heart pump 22 with the heart 25 of a patient.

Heart pump system 20 is illustrated in an exploded view. Accordingly, it should be understood that during implantation the cuff 24, or a portion thereof, may be attached to the heart 25 prior to coring. Heart 25 may be cored at a left ventricle (e.g., when providing LVAD support), a right ventricle (when providing RVAD support), or both (e.g., when providing BiVAD support). The opening in the heart 25 extends from an outer surface of the heart 25 to an inner surface of the heart 25.

Heart pump 22 may be a centrifugal pump in some embodiments. For example, heart pump 22 may be similar to the heart pump embodiments described in PCT Patent Publication PCT/US2015/019308 (the '308 application), the contents of which are incorporated herein by reference. The heart pump 22 may include a proximal housing 26 (e.g., for housing an impeller) and an inflow cannula 28 extending distally from the housing 26 for drawing blood from the heart 25 and into the pump 22. "Proximal" as used herein in certain embodiments is understood to mean away from the heart 25 and towards the skin line and "distal" as used herein is understood to mean toward the heart 25 (e.g., during implantation or once implanted). The heart pump 22 may further include an outlet 30 for delivering blood to the patient (e.g., via the aorta of the patient in a traditional LVAD configuration or a pulmonary artery in a traditional RVAD configuration). A percutaneous driveline cable 32 may be coupled the housing 26 which may deliver drive signals and/or power to the pump 22. Additionally, the pump 22 may include engagement features 23 (see FIG. 7 and FIG. 8) configured to facilitate mechanical coupling of the pump 22 to the cuff 24. The methods and devices for coupling the pump 22 to the cuff 24 may be similar to those described in the '308 application, previously incorporated by reference.

Figure 3:
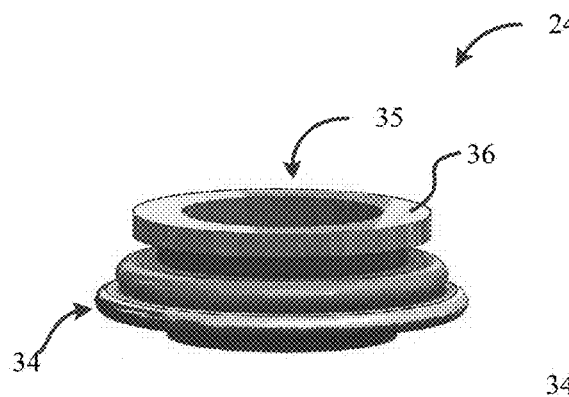
FIG. 3 illustrates the exemplary cuff of FIG. 2 according to some embodiments of the present disclosure.
Figure 4:
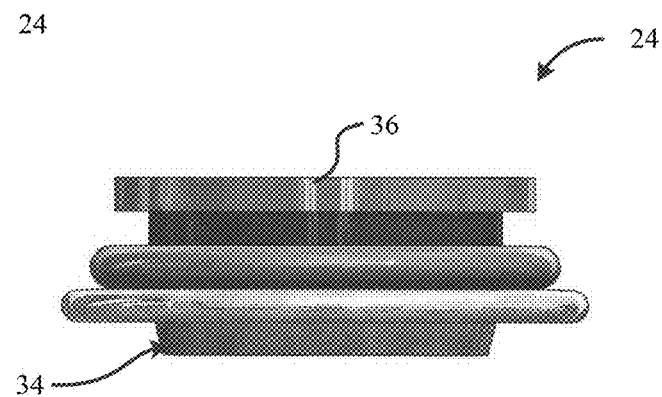
FIG. 4 illustrates a side view of the exemplary cuff of FIG. 2 according to some embodiments of the disclosure.
Figure 5:
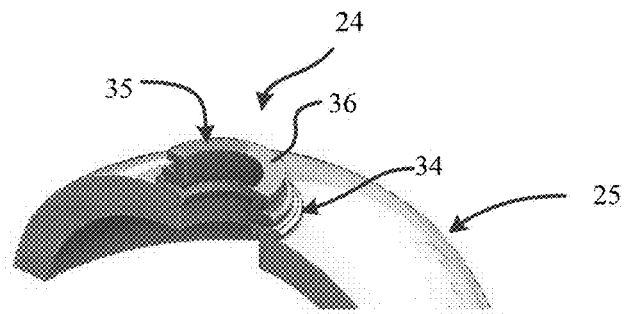
FIG. 5 illustrates a cut away view of the implanted cuff of FIG. 2 according to some embodiments of the disclosure.
Figure 6:
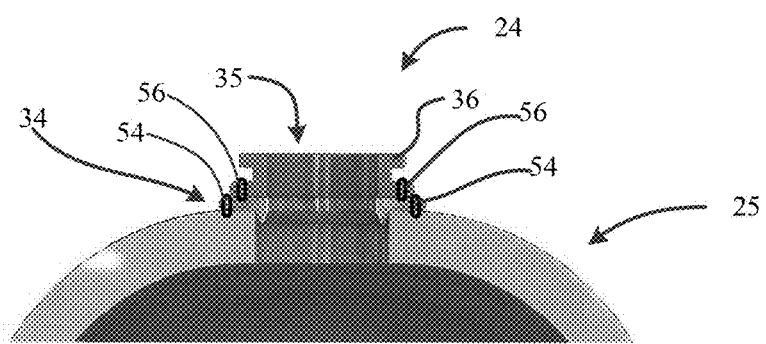
FIG. 6 illustrates a cross-sectional view of the implant cuff of FIG. 2 according to some embodiments of the disclosure.
Figure 7:
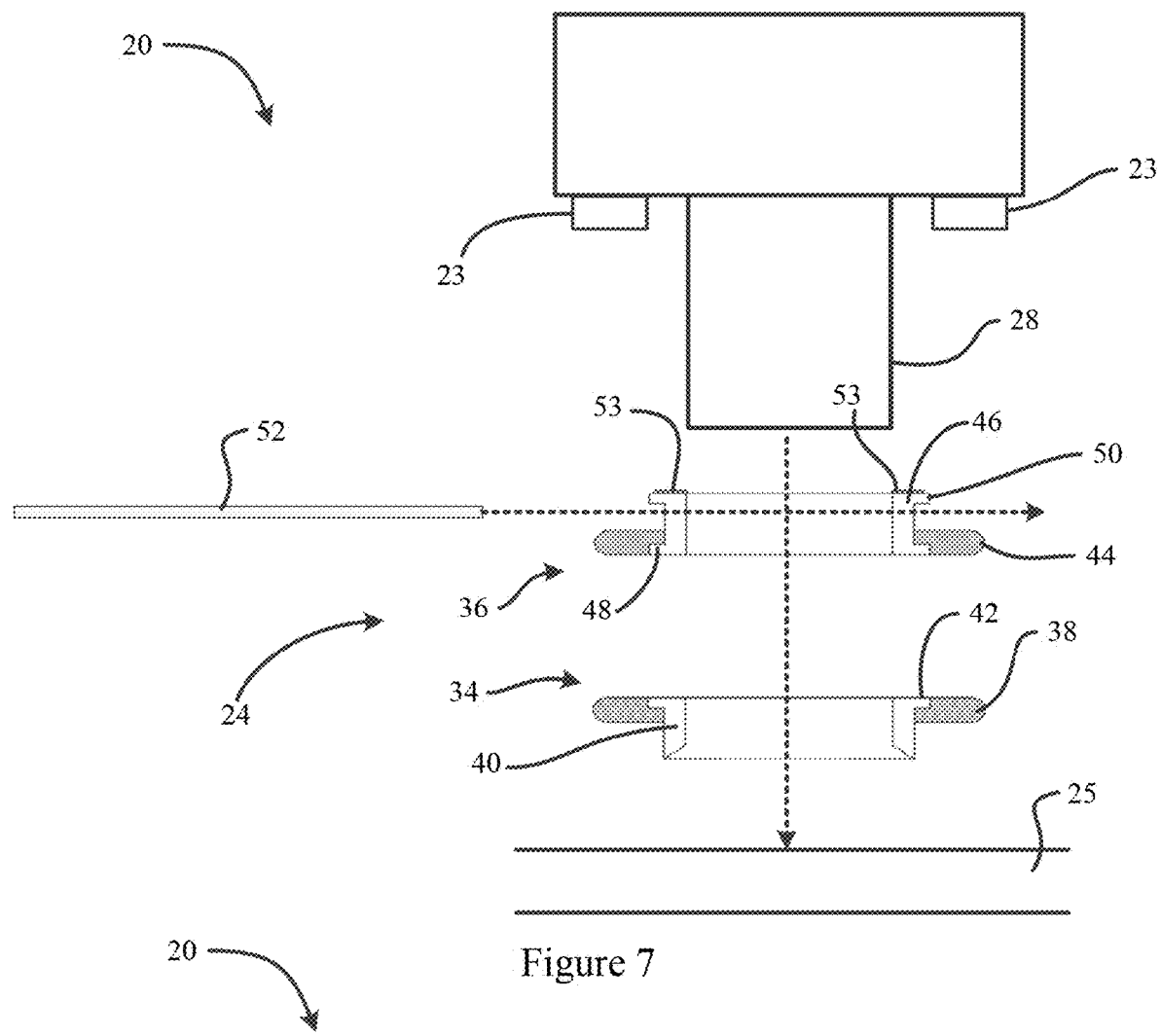
FIG. 7 illustrates an exploded cross-sectional view of the heart pump system of FIG. 2 according to some embodiments of the disclosure.
Figure 8:
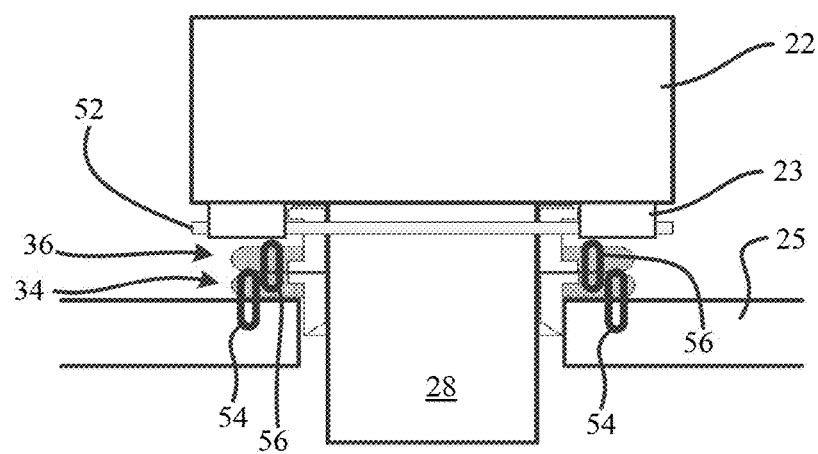
FIG. 8 illustrates an assembled view of the heart pump system of FIG. 2 according to some embodiments of the disclosure.

FIG. 3 illustrates the exemplary cuff 24 of FIG. 2 according to some embodiments of the present disclosure. FIG. 4 illustrates a side view of the exemplary cuff 24. FIG. 5 illustrates a cut away view of the implanted cuff 24 and FIG. 6 illustrates a cross-sectional view of the cuff 24. Additionally, FIG. 7 illustrates an exploded cross-sectional view of the heart pump system 20 and additional details of cuff 24. FIG. 8 illustrates an assembled view of the heart pump system 20 according to some embodiments of the disclosure.

As illustrated in FIGS. 3-8, the cuff 24 may comprise a cuff base 34 and a cuff port 36. The cuff 24 may define an opening 35 therethrough from a proximal side of cuff 24 to the distal side of cuff 24 to accommodate the inflow cannula 28 of heart pump 22 and/or a coring tool for creating the opening in the heart tissue when the cuff 24 or portion thereof is attached to the heart 25 prior to coring.

The cuff base 34 may comprise a flexible layer 38 coupled with a conduit 40, as best seen in FIG. 7 and FIG. 8. The flexible layer 38 may have a proximal surface and a distal surface and may define a portion of opening 35 of cuff 24. The distal surface of the flexible layer 38 may be configured to engage with the outer surface of the heart 25. In some embodiments, the flexible layer 38 comprises a blood absorbing (at least to a degree) and/or blood clotting material that may form a fluid seal with the tissue. In some embodiments, the flexible layer 38 may be a felt or textile material. Optionally, the flexible layer 38 may comprise PTFE, polyester, silicone, rubber, or other textile or any combination thereof. Additionally, the flexible layer 38 may be a velour, woven fabric/textile, or other configuration. In various embodiments, the flexible layer 38 may be a material that promotes tissue ingrowth. In some embodiments, the flexible layer 38 may be a material that promotes tissue attachment. In some embodiments, the flexible layer 38 may be a material that promotes a tissue-device interface. Optionally, the flexible layer 38 may be a graft material, e.g., DACRON, or other blood absorbing/clotting material. While the flexible layer 38 is illustrated as having a circular outer perimeter, it should be understood that the flexible layer 38 is not limited to the illustrated configuration with the circular outer perimeter. Other outer perimeter configurations are possible (e.g., rectangular or the like). The flexible layer 38 may have a thickness of 0.2 to 5.0 mm (e.g., between 0.5-4 mm, between 1-2 mm, or the like). The outer diameter of flexible layer 38 may be 10-70 mm in some embodiments, optionally 35-50 mm. In some embodiments, the flexible layer 38 may be dimensioned to extend laterally about 1-25 mm from the inlet cannula of the associated pump. In some embodiments, the flexible layer 38 may comprise multiple layers of fabric or textile (e.g., 2 or more). Further, optionally, the flexible layer 38 may include a silicone layer or other elastomer component. The silicone layer or elastomeric component may help provide the fluid seal between the cuff base 34 and the heart 25. In some embodiments, the flexible layer 38 comprises a plurality of materials. In some embodiments, the flexible layer 38 comprises a material to promote tissue ingrowth. The flexible layer 38 may comprise one or more other layers to promote tissue ingrowth, create the desired rigidity, control for infection, or other desired properties.

The conduit 40 may generally define a channel having a proximal opening and a distal opening and an axis extending therebetween. The channel may further include an inner surface and an outer surface opposite the inner surface. In some embodiments, the conduit 40 may be constructed of a rigid or semi-rigid material to direct flow or maintain the opening in the heart. The conduit 40 may be a rubber, plastic, or metal material, such as titanium. Optionally, as will be described in further detail below, the conduit 40 may be a flexible material in certain embodiments (e.g., fabric, textile, silicone, etc.). The channel of conduit 40 may be provided for receiving the inflow cannula 28 of the pump 22. In some embodiments, an outer surface of the inflow cannula 28 and the inner surface of the conduit channel may be dimensioned to fittingly mate.

The conduit 40 may be provided with a proximal lip 42 at a proximal portion of conduit 40. The proximal lip 42 may be provided as a location for mechanically coupling the conduit 40 with the flexible layer 38. For example, in some embodiments, the flexible layer 38 may be crimped, bonded, or sewn to the conduit 40 at the proximal lip 42 of conduit 40.

The conduit 40 may have a distal portion that extends distally relative to the distal surface of the flexible layer 38. At the distal end of conduit 40, an inner surface of the conduit 40 may gradually taper toward the outer surface of the conduit 40 (away from the axis) to form a beveled distal edge. In some embodiments, an outer surface of the conduit 40 may gradually taper outwardly (away from the axis) to form an outwardly tapered or flared distal end of conduit 40.

Additionally, in some embodiments, the outer surface of conduit 40 that projects distally from the distal surface of flexible layer 38 may have a powdered metal coating or may otherwise be textured (e.g., roughened) which may promote tissue ingrowth into the textured surface. The tissue ingrowth may prolong sealing and attachment of base 34 to the heart 25. The textured surface may promote endothelial layer formation and may limit thrombus from entering the blood stream. Accordingly, the textured surface may reduce the occurrence of stroke in patients.

The cuff port 36 may comprise an external flexible layer 44 coupled with a conduit 46, as best seen in FIG. 7 and FIG. 8. The flexible layer 44 may have a proximal surface and a distal surface and may define a portion of opening 35 of cuff 24. The distal surface of the flexible layer 44 may be configured to engage with the proximal surface of flexible layer 38. In some embodiments, the flexible layer 44 may be a felt or textile material (e.g., PTFE, polyester, or the like) or a rubber, silicone, or other elastomeric material or combinations thereof. Optionally, the flexible layer 44 may have a velour, non-woven, or woven configuration. Similar to flexible layer 38, it should be understood that while the flexible layer 44 is illustrated as having a circular outer perimeter, it should be understood that the flexible layer 44 is not so limited to such a design. In some embodiments, the flexible layer 44 may have a width or diameter that is less than a width or diameter of flexible layer 38, as illustrated in FIGS. 2-6. Optionally, the width or diameter of flexible layer 44 may be approximately equal to the width or diameter of flexible layer 38 as illustrated in FIG. 7 and FIG. 8. In still further embodiments, the width or diameter of flexible layer 44 may be greater than the width or diameter of flexible layer 38 such that a perimeter portion of flexible layer 44 overhangs from flexible layer 38. The overhanging portion of flexible layer 44 may be sewn separately to the heart 25 in some embodiments. The flexible layer 44 may have a thickness of 0.5 to 4.0 mm (e.g., between 1-2 mm or the like). In some embodiments, the flexible layer 44 may comprise multiple layers of material (e.g., 2 or more). Further, optionally, the flexible layer 44 may include a silicone layer or other elastomer component.

The conduit 46, similar to conduit 40, may generally define a channel having a proximal opening and a distal opening and an axis extending therebetween. In some embodiments, the conduit 46 may be constructed of a metal material, such as titanium. The channel of conduit 46 may be dimensioned similarly to conduit 40 and may be provided for receiving the inflow cannula 28 of the pump 22. The conduit 40 may be provided with a distal lip 48 at a distal portion of conduit 46. The distal lip 48 may be provided as a location for mechanically coupling the conduit 46 with the flexible layer 44. Similar to flexible layer 38, the flexible layer 44 may be crimped, bonded, or sewn to the conduit 46 at the distal lip 48 of conduit 46.

The conduit 46 may have a proximal portion that extends proximally relative to the proximal surface of the flexible layer 44. An engagement feature 50 may be provided on the proximal portion of conduit 46 that is configured to cooperate with a corresponding engagement feature of a heart pump (e.g., engagement feature 23 of heart pump 22 in FIG. 7 and FIG. 8). In the illustrated embodiments, the engagement feature 50 may be a lip that extends outwardly from the proximal end of the port 36. It should be understood that configuration is exemplary and non-limiting. The attachment of pump 22 to cuff 24 may take advantage of the techniques and components described in the '308 application. In some embodiments, a clip 52 may be delivered transverse to the cuff 24 to lock the engagement feature 50 of port 36 with the engagement feature 23 of pump 22, as illustrated in FIG. 7 and FIG. 8.

A proximal end of the conduit 46 may further include another flexible layer 53. The flexible layer 53 may be configured to be disposed between the port 36 and the pump 22 when the pump 22 and the port 36 are coupled to one another.

In some embodiments, the base 34 may be attached to the outer surface of the heart 25 before the heart 25 is cored to form the opening. For example, a surgeon may suture the base 34 to the surface of the heart 25 by applying sutures 54 through the flexible layer 38 and into the outer surface of the heart 25. After the base 34 is sutured in place the distal portion of the conduit 40 of base 34 may be pressed against the tissue surface. Thereafter, the surgeon may then core the heart 25 to form the opening in the heart 25 that extends from the outer surface of the heart 25 to the inner surface of the heart 25. The surgeon may form the opening by inserting a coring tool through the channel defined by conduit 40. As such, the coring tool may create an opening in the heart that is slightly smaller in diameter compared to the outer surface of the conduit 40 of base 34. However, the heart tissue may be flexible, especially once cored and may accommodate the distal portion of the conduit 40 of base 34 into the opening formed in the heart tissue by the coring tool in a fitted manner. After coring, blood may enter into the flexible layer 38 and may clot. Thereafter, there may be tissue ingrowth into the flexible layer 38 which may further limit blood leaking at the interface between the base 34 and the heart tissue. Additionally, the beveled distal edge of the conduit 40 may limit blood from entering the interface between the outer surface of the conduit 40 and the heart tissue once the base 34 is implanted and the heart 25 is cored by funneling blood toward the inner surface of the conduit 40. In some embodiments having an outwardly tapered or flared distal end of conduit 40, the tapered or flared distal end may push into the tissue at the distal end relative to more proximal portions of the distal end of conduit 40. This action may also further form a fitted engagement between the base 34 and the heart tissue to limit blood leaking.

The port 36 may be attached to the base 34 before or after attachment of the base 34 to the heart tissue. The port 36 may be attached to the heart tissue by applying suture 56 through the flexible layer 44 and into the flexible layer 38. Optionally, suture 56 may extend into heart tissue. The interface between the flexible layer 38 and the flexible layer 44 may clot the blood that enters the interface and may thereby seal the interface between flexible layer 38 and flexible layer 44 to prevent blood leakage at the interface.

After coring the heart and with the cuff 24 attached to the heart 25, the inflow cannula 28 of the pump 22 may then be inserted into the opening of the heart 25 through the opening 35 of the cuff. The pump 22 may then be coupled with the port 36 of the cuff 24 by engaging the engagement members 50 of the cuff 24 with the engagement members 23 of the pump. Once coupled, the flexible layer 53 may be disposed at the interface between the pump 22 and the cuff 24. The flexible layer 53 may receive blood at the interface and may cause the received blood to clot at the interface between the pump 22 and the cuff 24.

Accordingly, in some embodiments, a flexible layer (e.g., flexible layer 38, 44, 46) may be provided at each of the component-component interfaces (e.g., pump 22 to cuff 24, the base 34 to the port 36) or the component—tissue interfaces (e.g., the cuff 24 to the outer surface of the heart 25) to clot received blood and to form a seal at the interface thereby limiting blood leakage when the pump 22 is implanted.

Figure 9:
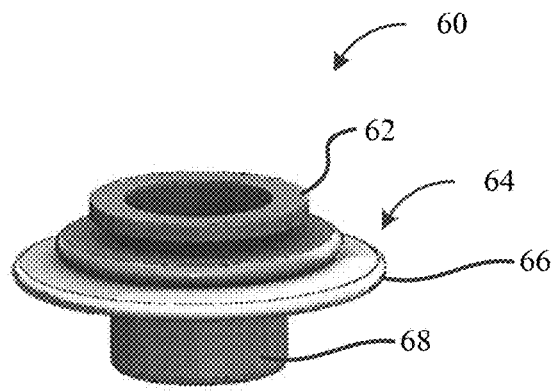
FIG. 9 illustrates another heart pump cuff according to some embodiments of the disclosure.
Figure 10:
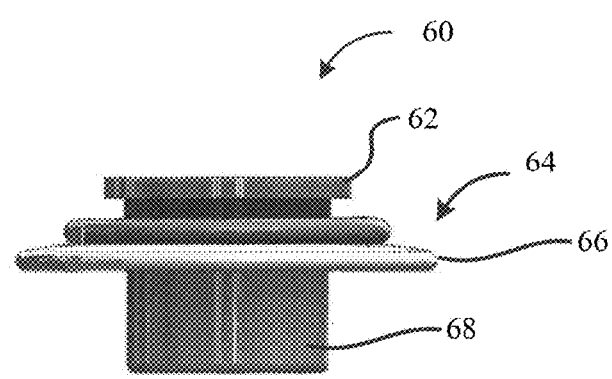
FIG. 10 illustrates a side view of the heart pump cuff of FIG. 9 according to some embodiments of the disclosure.
Figure 11:
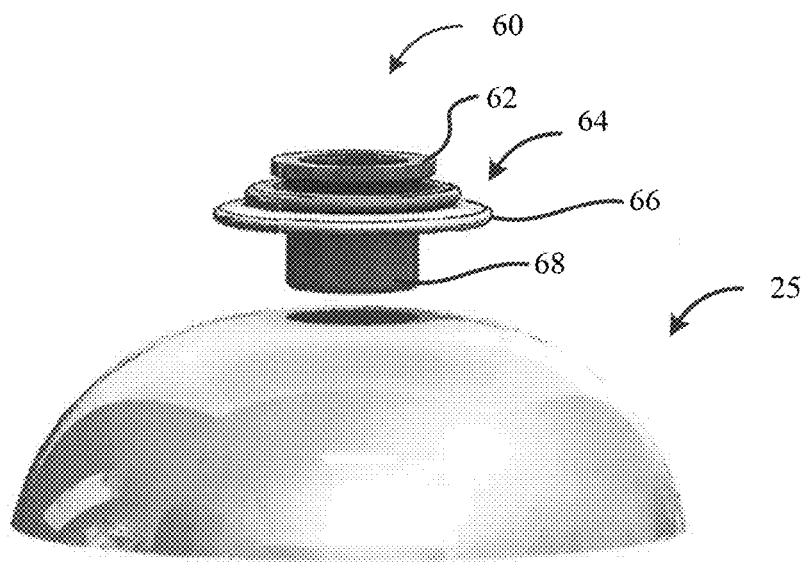
FIG. 11 illustrates the implantation of the heart pump cuff of FIG. 9 according to some embodiments of the disclosure.
Figure 12:
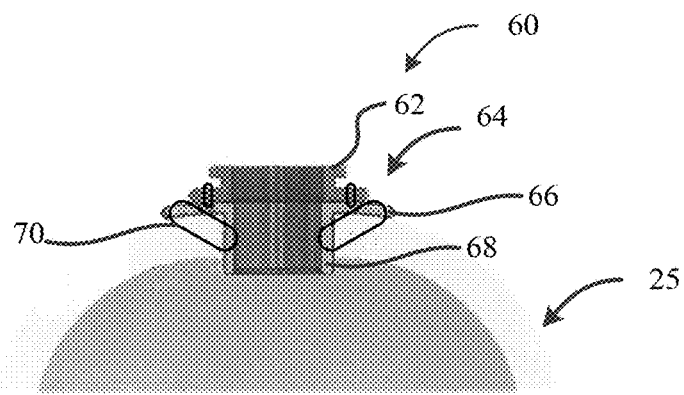
FIG. 12 illustrates a cross-sectional view of the implanted heart pump cuff of FIG. 9 according to some embodiments of the disclosure.

FIG. 9 illustrates another heart pump cuff 60 according to some embodiments of the disclosure. FIG. 10 illustrates a side view of the heart pump cuff 60 of FIG. 9. FIG. 11 illustrates the implantation of the heart pump cuff 60 and FIG. 12 illustrates a cross-sectional view of the implanted heart pump cuff 60. Cuff 60 may include a port 62 and a base 64. The port 62 may have a similar configuration as port 36 of cuff 24. Base 64 may comprise a primary flexible layer 66 coupled with a secondary flexible layer 68. The primary flexible layer 66 may have a proximal surface and a distal surface opposite the proximal surface. The distal surface of the primary flexible layer 66 may be configured to engage with an outer surface of the heart 25. The primary flexible layer 66 may have an opening therethrough for receiving an inflow cannula of a heart pump (e.g., cannula 28 of pump 22) or a coring tool. In some embodiments, the primary flexible layer 66 may be a lateral felt medium.

The secondary flexible layer 68 may be coupled with the primary flexible layer 66 about the opening in the primary flexible layer 66. When implanted, the secondary flexible layer 68 may protrude distally from the distal surface of the primary flexible layer 66. The secondary flexible layer 68 may form a conduit having an inner surface and an outer surface. The outer surface may be configured to engage with the ventricular bore (the walls forming the opening in the heart 25). The inner surface of the conduit formed by the secondary flexible layer 68 may be configured to receive the inflow cannula 28 of the pump 22. The inner surface may couple with the outside surface of the inflow cannula 28 in a close fitting arrangement. In some embodiments, the secondary flexible layer 68 may be a radial felt medium.

Similar to base 34, base 64 may be attached to the heart 25 prior to coring in some embodiments. Given the flexible nature of the flexible layers 66, 68, the secondary flexible layer 68 may be inverted or flipped such that it is positioned on a proximal side of the primary flexible layer 66 during attachment of the primary flexible layer 66 to the surface of the heart 25. After coring the opening in the heart 25, the secondary flexible layer 68 may be repositioned relative to the primary flexible layer 66 such that the secondary flexible layer 68 is positioned distally from the distal surface of the primary flexible layer 66 and into the ventricular bore of the heart 25. The flexible layers 66, 68 receive blood therein and the blood clots inside the flexible layers 66, 68 providing a seal therein.

The port 62 may be attached before or after attachment of the base 64. A flexible layer of the port 62 may be sutured onto the primary flexible layer 66 of the base 64. Thereafter, the heart pump 22 may be attached to the port 62 in a manner described above.

In some embodiments, the ventricular bore may be provided prior to attachment of the base 64. In such embodiments, the primary flexible layer 66 may be sewn onto the heart 25 with a suture 70 that extends through the primary flexible layer 66, through the heart tissue, and also through the secondary flexible layer 68, as illustrated in FIG. 12. The suture 70 may extend distally through the proximal surface of the primary flexible layer 66, through the distal surface of the primary flexible layer 66, into the outer surface of the heart 25, through the surface forming the opening in the heart 25, into the outer surface of secondary flexible layer 68, through the inner surface of the secondary flexible layer 68 and back through each surface to the proximal surface of the primary flexible layer 66. When installed, the secondary flexible layer 68 may act as an O-ring seal between the inflow cannula 28 of a pump 22 and the heart tissue.

Accordingly, in some embodiments, a flexible layer is provided in the core of the ventricle to provide better sealing and faster stabilization of the pump compared to devices with metal surfaces and only an external (i.e., on the outer myocardial surface) flexible material, such as an external felt sewing ring or the like. Without the secondary flexible layer 68, it may be difficult to form the seal at the core because of the soft flexible manner of the myocardium after coring. Thus, the radial felt seal formed by the secondary flexible layer 68, in addition to the lateral seal formed by primary flexible layer 66 may help reduce bleeding and leaks after installation.

Figures 13, 14:
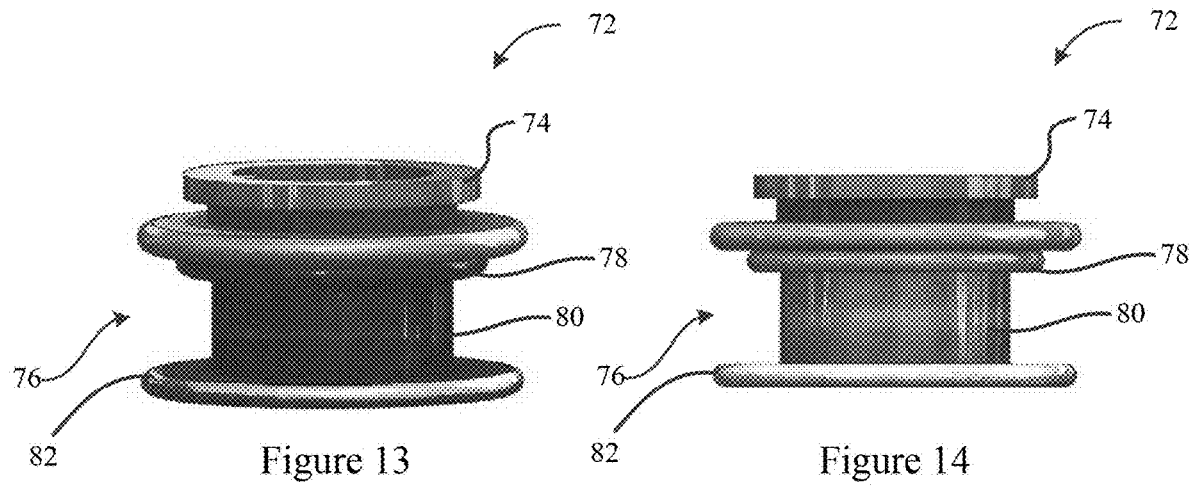
FIG. 13 illustrates yet another heart pump cuff according to some embodiments of the disclosure.
FIG. 14 illustrates a side view of the heart pump cuff of FIG. 13 according to some embodiments of the disclosure.
Figure 15:
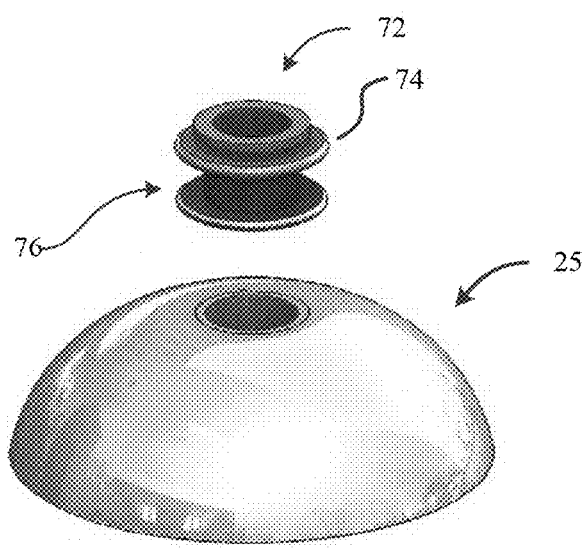
FIG. 15 illustrates the implantation of the heart pump cuff of FIG. 13 according to some embodiments of the disclosure.
Figure 16:
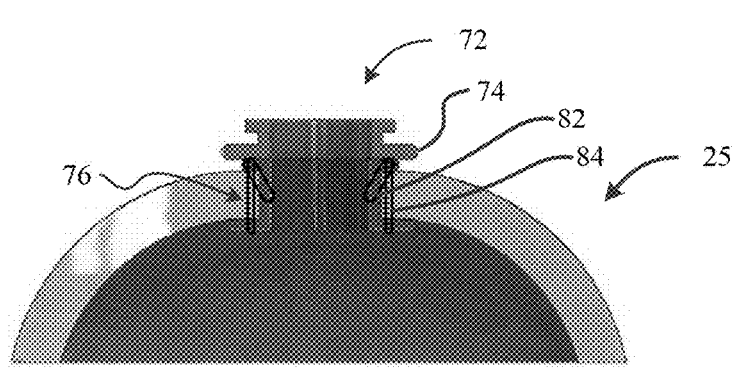
FIG. 16 illustrates a cross-sectional view of the implanted heart pump cuff of FIG. 13 according to some embodiments of the disclosure.

FIG. 13 illustrates yet another heart pump cuff 72 according to some embodiments of the disclosure. FIG. 14 illustrates a side view of the heart pump cuff 72. FIG. 15 illustrates the implantation of the heart pump cuff 72 and FIG. 16 illustrates a cross-sectional view of the implanted heart pump cuff 72. Pump cuff 72 may include a port 74 and a base 76. The port 74 may have a similar configuration as port 36 of cuff 24. The base 76 may include a primary flexible layer 78, a secondary flexible layer 80, and a tertiary flexible layer 82. The primary flexible layer 78 and the secondary flexible layer 80 may be similar to the primary flexible layer 66 and the secondary flexible layer 68 of base 64, respectively. The tertiary flexible layer 82 may be coupled with a distal end of the secondary flexible layer 80 and may extend radially away from the distal end of the secondary flexible layer 80. The tertiary flexible layer 82 may have a proximal surface and a distal surface. The proximal surface of tertiary flexible layer 82 may be configured to engage with an inner surface of the heart 25. Accordingly, the heart tissue may be sandwiched between the tertiary flexible layer 82 and the primary flexible layer 78 when the base 76 is implanted. Additionally, the secondary flexible layer 80 may be provided to border the ventricular bore.

In some embodiments, the base 76 may be attached to the heart 25 with one or more sutures 84 that extends from the primary flexible layer 78 through the heart tissue and through the tertiary flexible layer 82. Additionally, the base 76 may be attached to the heart 25 with one or more suture 86 that extends from the primary flexible layer 78 through the heart tissue and through the secondary flexible layer 80.

Figure 17:
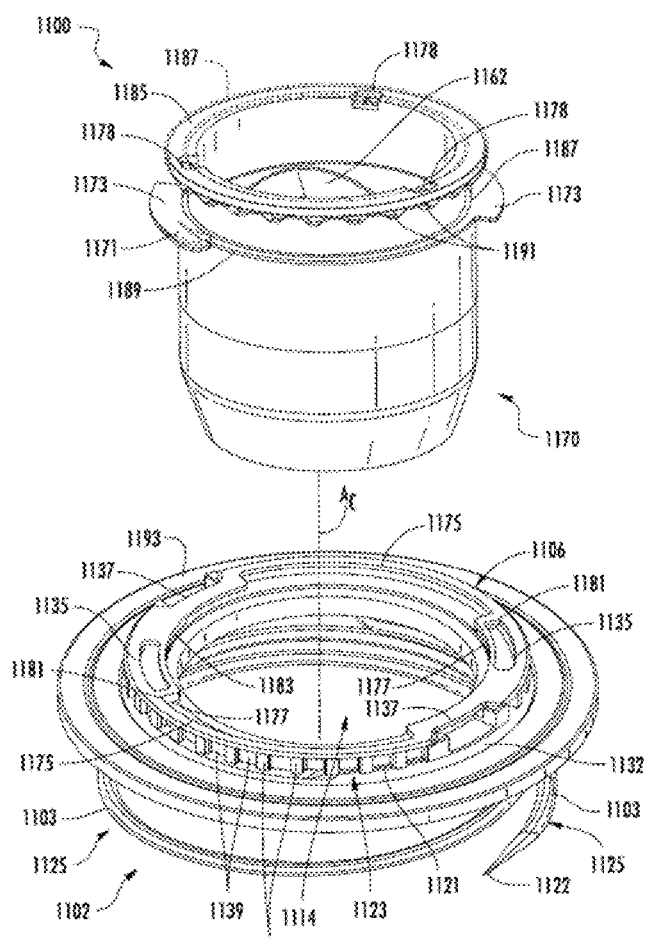
FIG. 17 illustrates yet another heart pump cuff according to some embodiments of the present disclosure.

PCT Application No. PCT/US2014/028346 (the '346 application), incorporated herein by reference in its entirety, describes various embodiments of a connector configured for implanting and using in a tissue wall to establish, maintain, control, and close a fluid communication between opposing surfaces of the tissue wall. FIG. 17 illustrates an exemplary connector 1100 according to some embodiments of the present disclosure. The connector 1100 may be configured to be secured in a heart wall (which also may be referred to as a "tissue wall") to facilitate in vivo implantation of a VAD and its attachment to the heart. The connector 1100 may include a cuff and a cannula 1170 having a hemostasis valve 1162, as shown, which features may correspond generally to those described with respect to the various embodiments of the '346 application, although certain differences are described herein below. The cuff may comprise a base 1102 and a port 1106. It will be appreciated that the connector 1100 may also include other features, such as a coupler device, configured in a manner similar to those described with respect to the various embodiments of the '346 application.

The base 1102 may be configured for advancing at least partially through the heart wall to secure the cuff thereto for subsequent implantation of a VAD. The port 1106 may be detachably or fixedly (i.e., rigidly) attached to a proximal portion of the base 1102 and may define a central aperture 1114 therethrough. In this manner, upon advancing a distal portion of the base 1102 at least partially through the heart wall, the port 1106 may be positioned against or near the heart wall and the aperture 1114 may provide access to the heart wall. The cannula 1170 may be configured for positioning through the aperture 1114 of the port 1106 and at least partially through the heart wall. The hemostasis valve 1162 may be disposed within the cannula 1170 and configured for controlling fluid communication therethrough. During use, the apical connector 1100 may be secured to the heart wall to facilitate in vivo implantation of the VAD and its attachment to the heart in a manner similar to that described with respect to the various embodiments of the '346 application.

The base 1102 may include a plurality of helical coils 1103 positioned about a central axis Ac of the connector 1100 and configured for advancing at least partially into the heart wall along respective helical paths defined by the coils 1103. For example, as shown in FIG. 17, the base 1102 may include two coils 1103 that are offset from one another and arranged in a generally symmetric manner about the central axis Ac of the connector 1100. In particular, the two coils 1103 may be attached to the port 1106 at attachment points 1121 that are spaced apart from one another, for example, by 180-degrees in a circumferential direction with respect to the central axis Ac of the connector 1100.

Distal tips 1122 (i.e., distal ends) of the two coils 1103 also may be spaced apart from one another, for example, by 180-degrees in a circumferential direction with respect to the central axis Ac of the connector 1100. In this manner, the coils 1103 may follow separate, opposing helical paths in the myocardial wall. In other embodiments, the base 1102 may include three or more coils 1103 that are offset from one another and arranged in a generally symmetric manner about the central axis Ac of the connector 1100, such that the coils 103 follow separate helical paths in the myocardial wall. The three or more coils 103 may include attachment points 1121 and distal tips 1122 that are equally spaced from one another in a circumferential direction with respect to the central axis Ac of the connector 1100. In various embodiments, the base 1102 may include two or more coils 1103 that are "clocked" (i.e., circumferentially spaced) from each other by 20 degrees, 25 degrees, 30 degrees, 45 degrees, 60 degrees, 90 degrees, or 120 degrees with respect to the central axis Ac of the connector 1100. As shown, the coils 1103 may have a radially-expanding helical shape (i.e., a conical shape) such that a helical diameter of the coil 1103 increases from the proximal end to the distal end of the coil 1103. Due to the radially-expanding helical shape, the coils 1103 may be configured to compress at least a portion of the heart wall inward toward the central axis Ac of the connector 1100 when the base 1102 is advanced through the heart wall. It will be appreciated from the description herein that the base 1102 may include other anchoring mechanisms (other than coils) common in the surgical field, such as clips, staples, and screws. In some embodiments, the base 1102 may include a combination of different anchoring mechanisms.

As compared to embodiments in which the base 1102 includes only a single coil 1103, the plurality of coils 1103 of the foregoing embodiments may improve stability of the port 1106 as well as the overall connector 1100 when secured in the heart wall. In particular, the plurality of coils 1103 may provide balanced engagement of the heart wall and prevent the port 1106 from lifting off of the heart wall (opposite the coil insertion point), as may be experienced with a single coil configuration of the base 1102. As will be appreciated, the plurality of coils 1103 may enhance initial starting and advancing of the base 1102 in the heart wall in a manner similar to that of a multi-start threadform. Additionally, as compared to a single coil configuration, the coils 1103 may be shorter, resulting in increased rigidity of the coils 1103, which may improve implantation consistency as well as full engagement feedback as the base 1102 is secured in the heart wall. Further, the balanced engagement provided by the plurality of coils 1103 may improve hemostasis achieved upon implantation of the connector 1100, for example by ensuring balanced contact between the port 1106 and the heart wall, or between an additional sealing element of the connector 1100 and the heart wall.

As shown in FIG. 17, each coil 1103 may include a proximal portion 1123 fixedly (i.e., rigidly) attached to the port 1106 and a distal portion 1125 extending distally away from the port 1106 and configured for advancing at least partially into the heart wall. The proximal portion 1123 may be disposed on a proximal side of a circumferential flange 1132 of the port 1106, and the distal portion 1125 may be disposed on a distal side of the flange 1132. In some embodiments, each coil 1103 may be attached to the port 1106 via one or more welds at the respective attachment point 1121. In particular, the proximal portion 1123 of the coil 1103 may be attached to the proximal surface of the flange 1132 via one or more welds therebetween at the respective attachment point 1121. According to this configuration, the one or more welds at the attachment point 1121 may be compressed upon extension of the distal portion 1125 of the coil 1103, as may be experienced during or after advancement of the distal portion 1125 into the heart wall. Such compression may limit loading on the one or more welds and enhance durability of the attachment point 1121 under fatigue, as may be experienced during use of the apical connector 1100 in the heart wall.

The port 1106 may be formed as a substantially ring-shaped member defining the central aperture 1114 therethrough and configured for positioning against or near the heart wall. As noted above, the port 1106 may be fixedly (i.e., rigidly) attached to the base 1102, in particular the proximal portions 1123 of the coils 1103. In this manner, axial rotation of the port 1106 results in corresponding axial rotation of the base 1102 for advancing the base 1102 at least partially into the tissue wall. The port 1106 may include one or more engagement features configured for engaging an instrument used to secure the port 1106 to the heart wall via the base 1102. For example, the port 1106 may include one or more engagement apertures 1135 (which also may be referred to as "engagement recesses") defined in the proximal end of the port 1106 and configured for receiving a mating feature of the instrument. Alternatively or additionally, the port 1160 may include one or more engagement notches 1137 (which also may be referred to as "engagement recesses") defined in the proximal end of the port 1106 along the circumferential outer surface thereof and configured for receiving a mating feature of the instrument.

The port 1106 also may include one or more engagement features configured for engaging an instrument used to stabilize the port 1106 after the port 1106 has been secured to the heart wall. For example, the port 1106 may include a plurality of engagement notches 1139 (which also may be referred to as "engagement recesses") defined in the circumferential outer surface of the port 1106 and configured for receiving a mating feature of the instrument. The notches 1139 may be configured for allowing the instrument to engage the port 1106 from a plurality of directions relative to the aperture 1114 of the port 1106 and the central axis Ac of the connector 1100. As shown, the notches 1139 may be arranged in a circumferential array along the circumferential outer surface of the port 1106 and may have a plurality of engagement tabs 1141 (which also may be referred to as "engagement protrusions") positioned therebetween. In other words, one of the engagement tabs 1141 may be positioned between each adjacent pair of the engagement notches 1139. In some embodiments, as shown, the notches 1139 may provide discrete engagement positions every 10 degrees about the circumferential outer surface of the port 1106. According to other embodiments, the notches 1139 may provide discrete engagement positions every 5 degrees, 15 degrees, 30 degrees, 45 degrees, or 90 degrees about the circumferential outer surface of the port 1106.

The cannula 1170 may be formed as a substantially tube-shaped member configured for positioning through the aperture 1114 of the port 1106 and at least partially through the heart wall. The cannula 1170 may include one or more features configured for releasably attaching the cannula 1170 to the port 1106. For example, as shown, the cannula 1170 may include one or more locking members 1171 (which also may be referred to as "locking arms" or "locking tabs") positioned near but offset from the proximal end of the cannula 1170 and extending along the outer circumferential surface of the cannula 1170. Each locking member 1171 may extend from a partial flange 1173 of the cannula 1170 and may be resilient or spring-like and configured to deflect from a natural position (as shown via dashed lines in FIG. 17) to a biased position (as shown via solid lines in FIG. 17) when a biasing force is applied thereto via mating features of the port 1106 as the cannula 1170 is attached to the port 1106. In some embodiments, in the natural position, the locking member 1171 may extend at least partially toward the proximal end of the cannula 1170 in an angled relationship with respect to the partial flange 1173, and in the biased position, the locking member 1171 may be deflected at least partially away from the proximal end of the cannula 1170 to or toward a coplanar relationship with the partial flange 1173.

The port 1106 may include one or more recesses 1175 defined in the proximal end of the port 1106 and configured to allow the locking members 1171 and the partial flanges 1173 to be inserted axially therein. The port 1106 also may include one or more undercut grooves 1177 defined near the proximal end of the port 1106 and extending along the inner circumferential surface of the port 1106. Each undercut groove 1177 may be positioned adjacent to and in communication with one of the recesses 1175. The undercut grooves 1177 may be configured to receive the partial flanges 1173 and the locking members 1171 of the cannula 1170 upon rotation of the cannula 1170 with respect to the port 1106. The cannula 1170 may include one or more engagement features configured for engaging an instrument used to position the cannula 1170 within the aperture 1114 of the port 1106 and rotate the cannula 1170 with respect to the port 1106. For example, the cannula 1170 may include a plurality of engagement notches 1178 (which also may be referred to as "engagement recesses") defined in the proximal end of the cannula 1170 and configured for receiving a mating feature of the instrument. In some embodiments, as shown, the engagement notches 1178 may extend to the inner circumferential surface of the cannula 1170. In other embodiments, the engagement notches 1178 may extend to the outer circumferential surface of the cannula 1170. Certain embodiments of an instrument that may be used to position the cannula 1170 within the aperture 1114 of the port 1106 and rotate the cannula 1170 with respect to the port 1106 are described herein below.

The port 1106 further may include one or more locking protrusions 1181 (which also may be referred to as "locking tabs") and one or more stop protrusions 1183 (which also may be referred to as "stop tabs"). The locking protrusions 1181 may be configured to deflect the locking members 1171 of the cannula 1170 distally (i.e., away from the proximal end of the cannula 1170) from their natural position upon rotation of the cannula 1170 with respect to the port 1106 in a first direction, such as a clockwise direction when viewed from the proximal end of the connector 1100. The stop protrusions 1183 may be configured to contact the locking members 1171 and/or the partial flanges 1173 and limit rotation of the cannula 1170 with respect to the port 1106 in the first direction. The locking members 1171 may be configured to return to or toward their natural position after advancing past the locking protrusions 1181, such that the locking members 1171 and the locking protrusions 1181 cooperate to prevent rotation of the cannula 1170 with respect to the port 1106 in an opposite second direction, such as a counter clockwise direction when viewed from the proximal end of the connector 1100. In this manner, the mating features of the cannula 1170 and the port 1106 may form a partial-turn locking mechanism configured to prevent the cannula 1170 from being detached from the port 1106 unless the locking members 1171 are biased by a user to disengage the locking protrusions 1181. According to the embodiment shown in FIG. 17, the partial-turn locking mechanism is a ¼-turn locking mechanism, although other configurations are possible, such as a ⅓-turn or a ½-turn configuration.

As compared to some other connector embodiments, the partial-turn locking mechanism of the connector 1100 provides a manner for locking the cannula 1170 to the port 1106, which may improve the structural integrity of the connector 1100 as well as the hemostasis achieved upon implantation of the connector 1100. Moreover, the partial-turn locking mechanism provides tactile feedback as the cannula 1170 is attached to the port 1106.

The partial-turn locking mechanism of the connector 1100 may be released to allow the cannula 1170 to be detached from the port 1106. In particular, the partial-turn locking mechanism may be released by inserting portions of an instrument through the engagement apertures 1135 of the port 1106 and biasing the locking members 1171 of the cannula 1170 distally such that the locking members 1171 disengage the locking protrusions 1181. Such disengagement of the locking members 1171 and the locking protrusions 1181 may allow the cannula 1170 to be rotated in the second direction and then axially removed from the port 1106. Certain embodiments of an instrument that may be used to release the partial-turn locking mechanism are described in PCT Application No. PCT/US2015/019308 (the '308 application) and referred to therein as a cannula release tool. As described, the cannula release tool may include a pair of prongs. It will be appreciated that the prongs may be inserted through the engagement apertures 1135 of the port 1106 to bias the locking members 1171 of the cannula 1170 distally such that the locking members 1171 disengage the locking protrusions 1181, thereby allowing the cannula 1170 to be rotated in the second direction and then axially removed from the port 1106.

The cannula 1170 may include one or more features configured for facilitating attachment of a VAD to the apical connector 1100. For example, as shown, the cannula 1170 may include a proximal flange 1185 (which also may be referred to as a "proximal lip") positioned at or near the proximal end of the cannula 1170 and extending along the outer circumferential surface of the cannula 1170. The cannula 1170 also may include an elastomer covering 1187 molded over a portion of the cannula 1170. The elastomer covering 1187 may extend from the proximal end of the cannula 1170 to an intermediate flange 1189 (which also may be referred to as an "intermediate lip"). As shown, the partial flanges 1173 may be attached to and coplanar with the intermediate flange 1189. In other embodiments, the intermediate flange 1189 may be offset from the partial flanges 1173. As shown, the elastomer covering 1187 may extend partially over the engagement notches 1178 along the proximal end of the cannula 1170, which may facilitate retention of mating features of an instrument within the engagement notches 1178 during positioning of the cannula 1170 with respect to the port 1106. In some embodiments, the elastomer covering 1187 may extend partially into the engagement notches 1178, which also may facilitate retention of mating features of the instrument. The elastomer covering 1187 may include a plurality of ridges 1191 defined in the circumferential outer surface of the elastomer covering 1187, positioned distally with respect to the proximal flange 1185 and extending toward the distal end of the cannula 1170.

When the cannula 1170 is attached to the port 1106, a circumferential groove or gap may exist between the proximal flange 1185 and the proximal end of the port 1106. The circumferential groove may be configured to receive a mating portion of a locking mechanism, such as a clip, for attaching a VAD to the connector 1100. In some embodiments, the mating portion of the locking mechanism, such as the clip, may include features configured to engage the ridges 1191 and thereby limit rotation of the locking mechanism and the VAD relative to the cannula 1170 and the overall connector 1100. Certain embodiments of locking mechanisms that may be used to attach a VAD or heart pump to a ventricular cuff are described in the '308 application. It will be appreciated that a proximal portion of the cannula 1170, including the proximal flange 1185, the elastomer covering 1187, the intermediate flange 1189, and the ridges 1191 thereof, may be configured in a manner similar to corresponding features of the various embodiments of cuffs described in the '308 application. In this manner, the cannula 1170 and the overall connector 1100 may be configured for attachment of a VAD via one or more of the embodiments of locking mechanisms described in the '308 application.

As shown in FIG. 17, the apical connector 1100 may include a sewing ring 1193 extending outwardly from the port 1106. The sewing ring 1193 may extend about the outer perimeter of the port 1106 and may be configured for suturing to the heart wall. The sewing ring 1193 may be made of a porous material, such as PTFE felt. Certain embodiments of sewing rings used as a part of ventricular cuffs are described in the '308 application. The sewing ring 1193 of the connector 1100 may have features and characteristics similar to those of the various embodiments of sewing rings described in the '308 application and may be attached to the port 1106 using attachment features and/or methods similar to those described therein.

Figure 18:
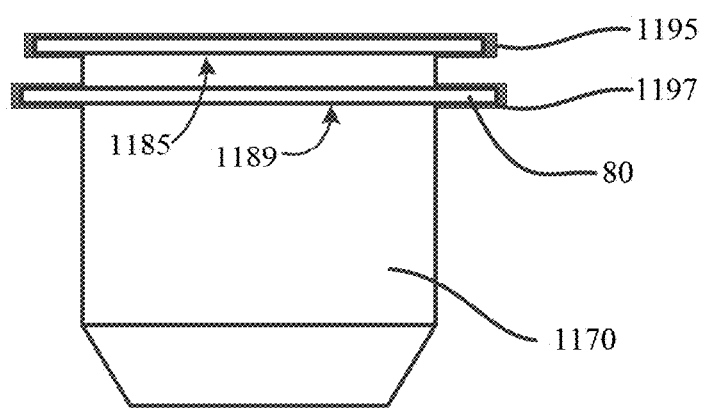
FIG. 18 illustrates a side view of the port of the heart pump cuff of FIG. 17 according to some embodiments of the present disclosure.

Additionally, to limit blood leaking at the interfaces between the cannula 1170 and the port 1106 and/or between the cannula 1170 and a VAD, one or more flexible layers similar to those described above may be provided. For example, FIG. 18 illustrates a side view of the cannula 1170 of connector system 1100 of FIG. 17 according to some embodiments of the present disclosure. In some embodiments, the proximal flange 1185 may include a flexible covering 1195 at a proximal surface of the proximal flange 1185. While the base attaches the pump to the myocardial wall upon insertion, it may be desirable to provide additional anchoring and/or sealing. For example, there may be initial sheath bleeding around the port until the blood clots or tissue grows into the appropriate areas. The flexible material provides faster sealing than metallic and other materials. Optionally the flexible covering 1195 may be disposed about the proximal flange 1185 such that the flexible material covers the proximal surface, outer side surface, and a portion of the distal surface of proximal flange 1185. The flexible covering 1195 may soak up excess blood at the interface between the pump and the proximal end of the cannula 1170 when the pump and cannula 1170 are engaged. The blood soaked up by the flexible layer 1195 may clot and thereby help seal the interface between the cannula 1170 and the pump against blood leakage.

Moreover, the intermediate flange 1189 and/or the locking members 1171 may also include a flexible layer 1197 at a distal surface of the flange 1189 and/or locking members 1171. Optionally, the flexible layer 1197 may be provided over the proximal surface of the flange 1198 and/or the proximal surface of the locking members 1171. Similar to the concepts described above, the flexible material may be provided to soak up blood at the interface between the cannula 1170 and the port 1106.

While the cannula 1170 is illustrated as including additional flexible layers 1195, 1197, it should be understood that in some embodiments, the flexible layers may be provided with the engagement feature of the pump and/or the port 1106 in addition to or in the alternative to the flexible layers 1195, 1197 on the cannula 1170. Optionally, the flexible layers used with cannula 1170 and/or port 1106 may comprise PTFE, polyester, silicone, rubber, or other textile or any combination thereof. Additionally, the flexible layers may be a velour, woven fabric/textile, or other configuration. Optionally, the flexible layers may be a graft material, e.g., DACRON, or other blood absorbing/clotting material.

The subject matter of the present invention is described here with specificity, but the claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method of coupling a heart pump to a heart of a patient, the method comprising:
   suturing a base to the heart such that a distal surface of a flexible layer of the base directly engages an outer surface of the heart, the base comprising a conduit that is coupled with the flexible layer, wherein the conduit comprises a distal portion that extends distally relative to the distal surface of the flexible layer, wherein an outer surface of the distal portion of the conduit comprises a powdered metal coating or a textured surface to promote tissue ingrowth into the textured surface;
   coupling a port to the base such that a lumen of the port is in alignment with the conduit;
   inserting a cannula of the heart pump through the conduit; and
   coupling the heart pump to an engagement feature of the port.

2. The method of claim 1, wherein the flexible layer comprises a material that promotes tissue ingrowth.

3. The method of claim 1, further comprising coring an opening in the heart after the base is sutured to the heart.

4. The method of claim 1, wherein the conduit comprises a metal material and wherein the conduit is sewn, bonded, or crimped to the flexible layer.

5. The method of claim 1, wherein the flexible layer comprises one or both of a felt material or a graft material.

6. The method of claim 1, wherein coupling the port to the base comprises suturing the port to the flexible layer of the base.

7. The method of claim 1, wherein an inner surface of the conduit tapers away from a central axis of the conduit and toward an outer surface of the conduit at a distal end of the conduit to form a beveled distal edge of the conduit.

8. The method of claim 1, wherein an outer surface of the conduit tapers away from a central axis of the conduit at a distal end of the conduit to form a flared distal end.

9. The method of claim 1, wherein the conduit comprises a flexible material.

10. The method of claim 9, wherein the base further comprises a distal flexible layer coupled with a distal end of the conduit, the distal flexible layer configured to engage with an inner surface of the heart disposed about a cored opening in the heart.

11. The method of claim 10, wherein suturing the base to the heart comprises suturing through the flexible layer, through the outer surface of the heart, through the inner surface of the heart and through the distal flexible layer.

12. The method of claim 1, wherein the port further comprises a flexible layer and wherein coupling the port to the base comprises suturing the flexible layer of the port to the flexible layer of the base.

13. The method of claim 1, wherein the engagement feature further comprises a flange that is retainable by a corresponding engagement feature of the heart pump.

14. The method of claim 1, wherein the distal portion of the conduit enters at least partially into the outer surface of the heart.

15. A method of coupling a heart pump to a heart of a patient, the method comprising:
   coring an opening in the heart;
   suturing a base to the heart such that a distal surface of a flexible layer of the base directly engages an outer surface of the heart, the base comprising a conduit that is coupled with the flexible layer, wherein the conduit comprises a distal portion that extends distally relative to the distal surface of the flexible layer and comprises a flexible material, wherein suturing the base to the heart comprises suturing through the flexible layer, through the outer surface of the heart, through the surface of the heart formed after coring the heart, and through the flexible conduit;

coupling a port to the base such that a lumen of the port is in alignment with the conduit;

inserting a cannula of the heart pump through the conduit; and coupling the heart pump to an engagement feature of the port.

16. The method of claim 15, wherein the conduit comprises a metal material and wherein the conduit is sewn, bonded, or crimped to the flexible layer.

17. The method of claim 15, wherein the flexible layer comprises one or both of a felt material or a graft material.

18. The method of claim 15, wherein the flexible layer comprises a material that promotes tissue ingrowth.

19. The method of claim 15, wherein an inner surface of the conduit tapers away from a central axis of the conduit and toward an outer surface of the conduit at a distal end of the conduit to form a beveled distal edge of the conduit.

20. A method of coupling a heart pump to a heart of a patient, the method comprising:

suturing a base to the heart such that a distal surface of a flexible layer of the base directly engages an outer surface of the heart, the base comprising a conduit that is coupled with the flexible layer, wherein the conduit comprises a distal portion that extends distally relative to the distal surface of the flexible layer;

coupling a port to the base such that a lumen of the port is in alignment with the conduit;

inserting a cannula of the heart pump through the conduit; and coupling the heart pump to an engagement feature of the port, wherein the heart pump further comprises an engagement feature corresponding with the engagement feature of the port, and wherein a flexible layer is disposed between the engagement feature of the heart pump and the engagement feature of the port when the heart pump is coupled with the engagement feature of the port.

* * * * *